(12) United States Patent
Hsiao et al.

(10) Patent No.: US 9,834,533 B2
(45) Date of Patent: Dec. 5, 2017

(54) PROCESS FOR PREPARING SGLT2 INHIBITORS AND INTERMEDIATES THEREOF

(71) Applicant: ScinoPharm Taiwan, Ltd., Tainan (TW)

(72) Inventors: Tsung-Yu Hsiao, Kaohsiung (TW); Jyh-Hsiung Liao, Kaohsiung (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 15/430,409

(22) Filed: Feb. 10, 2017

(65) Prior Publication Data

US 2017/0240520 A1   Aug. 24, 2017

Related U.S. Application Data

(60) Provisional application No. 62/297,687, filed on Feb. 19, 2016.

(51) Int. Cl.
*C07D 309/10* (2006.01)
*C07D 407/12* (2006.01)

(52) U.S. Cl.
CPC ......... *C07D 309/10* (2013.01); *C07D 407/12* (2013.01)

(58) Field of Classification Search
None
See application file for complete search history.

(56) References Cited

U.S. PATENT DOCUMENTS 6,414,126 B1 * 7/2002 Ellsworth .............. A61K 31/70 536/1.11
6,515,117 B2 * 2/2003 Ellsworth .............. A61K 31/70 536/1.11

* cited by examiner

*Primary Examiner* — Zinna Northington Davis
(74) *Attorney, Agent, or Firm* — Hamilton, DeSanctis & Cha, LLP; Sam L. Nguyen

(57) ABSTRACT

The present invention provides processes for preparing SGLT2 inhibitors, such as dapagliflozin and empagliflozin.

13 Claims, 1 Drawing Sheet

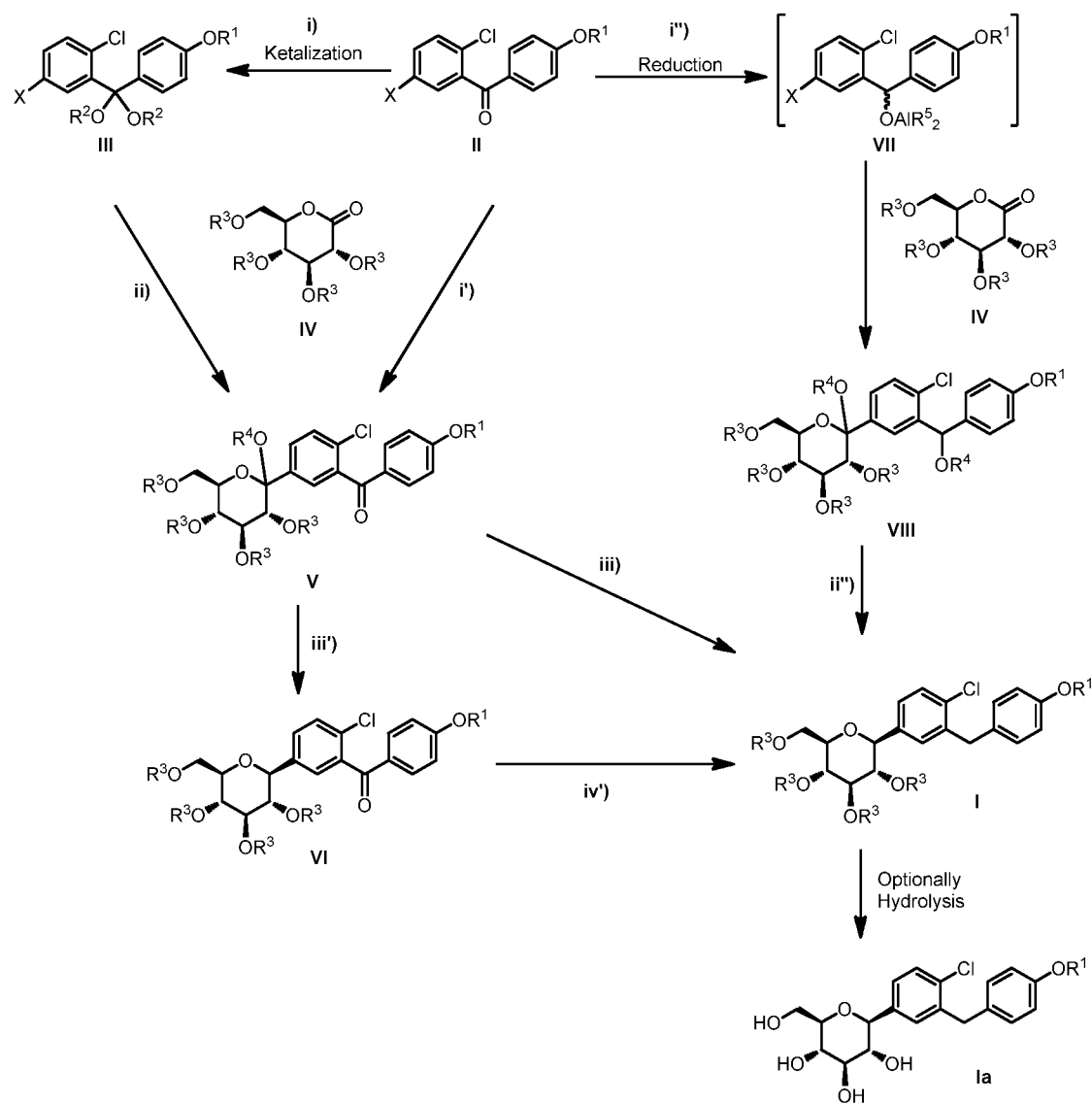

PROCESS FOR PREPARING SGLT2 INHIBITORS AND INTERMEDIATES THEREOF

CROSS-REFERENCES TO RELATED APPLICATIONS

This application claims priority to U.S. Provisional Application No. 62/297,687 filed Feb. 19, 2016, the complete disclosure of which is incorporated by reference herein.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Diabetes mellitus is a serious and chronic metabolic disease that is characterized by high blood glucose (hyperglycemia) and affects millions of people world-wide. SGLT2 is a Sodium-dependent GLucose co-Transporter protein which affects the reabsorption of glucose in the kidney. It is estimated that 90% of renal glucose reabsorption is facilitated by SGLT2. Since glucose reabsorption is mediated predominantly by SGLT2 and because high glucose levels have been identified as a cause of disease in diabetes, SGLT2 has become a drug target for type 2 diabetes therapy. Selective inhibition of SGLT2 has the potential to reduce hyperglycemia by inhibiting glucose reabsorption in the kidney with elimination of glucose by excretion in the urine (glucosuria).

A significant number of SGLT2 inhibitors are currently in clinical development and a significant portion of these are β-C-arylglucosides. Further, a series of therapeutically effective β-C-glucosides (i.e., canagliflozin, dapagliflozin, ipragliflozin and empagliflozin) that are Sodium-coupled GLucose co-Transporter 2 (SGLT2) inhibitors have recently received marketing approval for the treatment of diabetes mellitus.

Among the β-C-arylglucosides as SGLT2 inhibitors, it is noted that dapagliflozin and empagliflozin share the same core structure and differ only in the O-substitution of terminal phenoxy group, which makes both feasible to manufacture in single synthetic route(s).

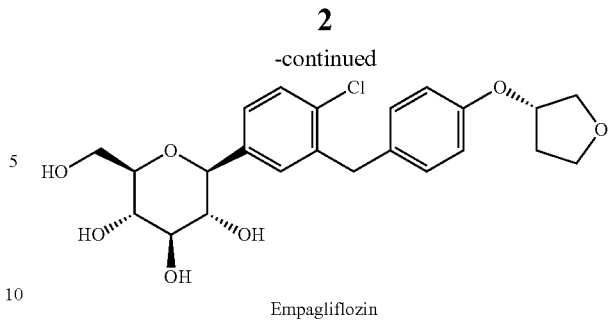

Empagliflozin

Dapagliflozin (trade name Farxiga) was developed by Bristol-Myers Squibb in partnership with AstraZeneca. The FDA approved dapagliflozin for glycemic control, along with diet and exercise, in adults with type 2 diabetes on Jan. 8, 2014. Dapagliflozin is chemically named as (2S,3R,4R,5S,6R)-2-[4-chloro-3-(4-ethoxybenzyl)phenyl]-6-(hydroxymethyl)tetrahydro-2H-pyran-3,4,5-triol.

Empagliflozin (trade name Jardiance) was developed by Boehringer Ingelheim and Eli Lilly and Company, and approved for the treatment of type 2 diabetes in adults in 2014. Empagliflozin is chemically named as (2S,3R,4R,5S,6R)-2-[4-chloro-3-[[4-[(3S)-oxolan-3-yl]oxyphenyl]methyl]phenyl]-6-(hydroxymethyl)oxane-3,4,5-triol. Both empagliflozin and dapagliflozin are inhibitors of the sodium glucose co-transporter-2 (SGLT-2), which causes sugar in the blood to be excreted by the kidneys and eliminated in urine.

A series of synthetic methods have been reported in the literature that can be used for the preparation of dapagliflozin and empagliflozin. For example, U.S. Pat. No. 6,414,126, U.S. Pat. No. 6,515,117 and WO 2004/063209 disclose similar synthetic route and intermediates for preparing dapagliflozin. WO 2005/092877, WO 2006/120208, WO 2011/039108 and WO 2015/101916 disclose various approaches and intermediates for preparing empagliflozin.

There is a need for novel and efficient process for the preparation of β-C-arylglucosides. This invention addresses those needs.

BRIEF SUMMARY OF THE INVENTION

Therefore a continuing need exists for novel and efficient methods for the preparation of β-C-arylglucosides, particularly dapagliflozin and empafliflozin. The following embodiments, aspects and variations thereof are exemplary and illustrative and are not intended to be limiting in scope.

In one aspect, the present invention provides a process for the preparation of a compound of formula V,

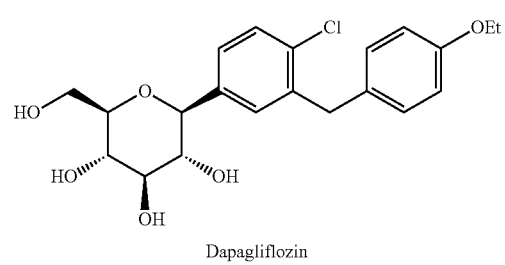

Dapagliflozin

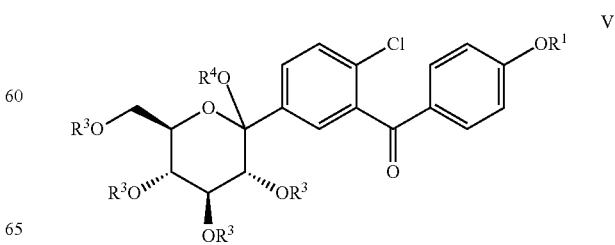

V comprising the steps of:
    i) converting a compound of formula II

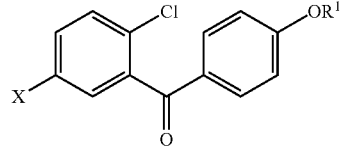

to a compound of formula III

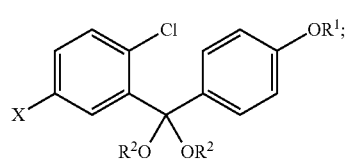

and
    ii) contacting a compound of formula III with a compound of formula IV

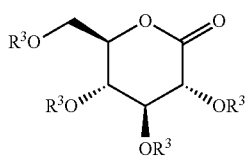

to form compound of formula V;
or
    i') contacting a compound of formula II with a compound of formula IV to form a compound of formula V
wherein
    X is a halogen;
    $R^1$ is selected from the group consisting of (3S)-tetrahydro-3-furanyl, (3R)-tetrahydro-3-furanyl and $C_1$-$C_{10}$ alkyl;
    $R^2$ is $C_1$-$C_{10}$ alkyl or can be taken together to form an optionally substituted 5-7 member cyclic ring;
    $R^3$ is hydrogen or a hydroxyl protecting group; and
    $R^4$ is $C_1$-$C_{10}$ alkyl.
    In a second aspect, the present invention further comprises converting the compound of formula V to a compound of formula I

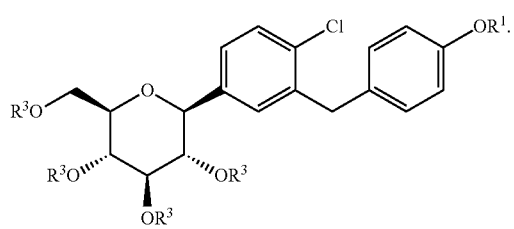

In a third aspect, the present invention further comprises
    iii) converting compound of formula V to compound of formula VI

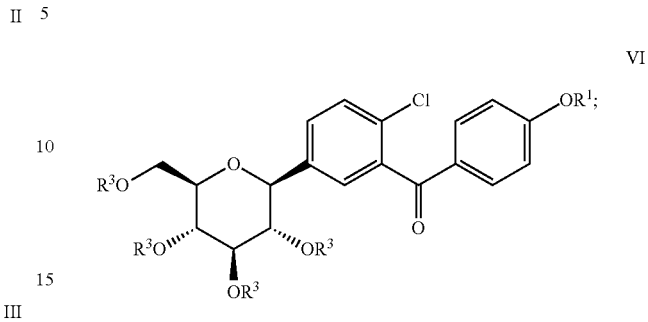

and
    iv) converting compound of formula VI to compound of formula I.
    In a fourth aspect, the present invention provides a process for the preparation of a compound of formula I

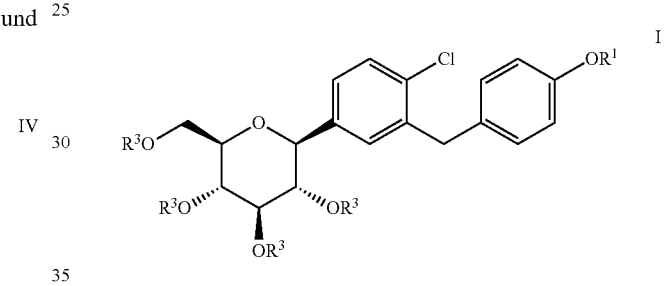

comprising the steps of:
    i'') converting a compound of formula II

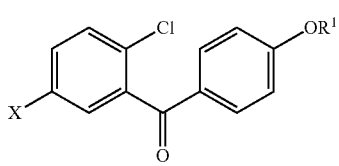

to a compound of formula VII

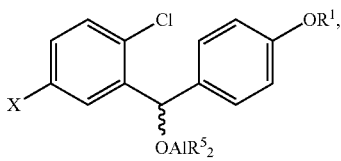

and
    converting the compound of formula VII to a compound of formula VIII

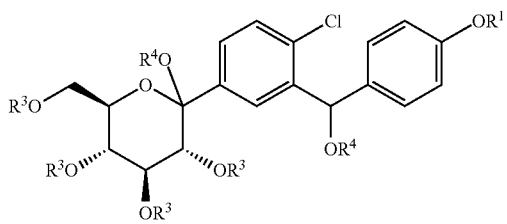

VIII in a one-pot reaction; and ii") converting the compound of VIII to compound of formula I wherein X is a halogen;

$R^1$ is selected from the group consisting of (3S)-tetrahydro-3-furanyl, (3R)-tetrahydro-3-furanyl and $C_1$-$C_{10}$ alkyl;

$R^3$ is hydrogen or hydroxyl protecting group; and $R^4$ and $R^5$ are $C_1$-$C_{10}$ alkyl.

In a fifth aspect, the present invention further comprises converting the compound of formula I to compound of formula Ia

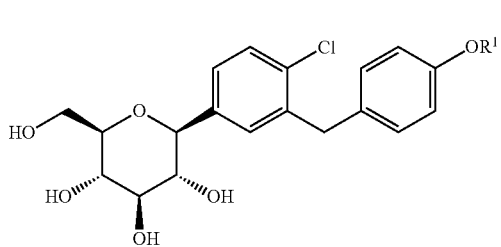

Ia where for the compound of formula I, $R^3$ is not hydrogen.

BRIEF DESCRIPTION OF THE DRAWINGS

FIG. 1 provides a scheme showing various synthetic routes for the preparation of dapagliflozin and empagliflozin.

DETAILED DESCRIPTION OF THE INVENTION

Definitions

As used herein, the term "glycoside" refers to a carbohydrate derivative wherein the carbohydrate is bound to a non-carbohydrate moiety (called an aglycone).

As used herein, the term "glucoside" refers to a glucose derivative wherein glucose is bound to a non-carbohydrate moiety (called an aglycone). A glucoside is a subset of the family glycoside.

As used herein, the term "C-glycoside" refers to a carbohydrate derivative, including a glucose derivative (so would be referred to as a "C-glucoside"), wherein the carbohydrate is bound to a non-carbohydrate moiety and the carbohydrate is bound to the non-carbohydrate moiety via a carbon-carbon covalent bond.

As used herein, the term "C-arylglycoside" refers to a carbohydrate derivative, including a glucose derivative (so would be referred to as a "C-arylglucoside"), wherein the carbohydrate is bound to an aromatic moiety via a carbon-carbon covalent bond.

As used herein, the prefix α- and β-refer to the configuration of the anomeric center of the C-arylglycoside. In the β-C-arylglycoside, the aryl group (i.e., the aglycone) is in the same relative positive with respect to the other chemical bonds at the anomeric center as the hydroxyl group is in β-glucose. In the α-C-arylglycoside, the aryl group (i.e., the aglycone) is in the same relative positive with respect to the other chemical bonds at the anomeric center as the hydroxyl group is in α-glucose.

As used herein, the term "SGLT2" refers to sodium/glucose cotransporter 2, which is a sodium-dependent glucose transport protein. SGLT2 is the primary co-transporter involved in renal glucose reabsorption. As used herein, "SGLT2 inhibitor" refers to any molecule that can modulate SGLT2 activity in vitro or in vivo.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "one-pot reaction" refers to a reaction in which a starting material or an intermediate compound undergoes at least two sequential chemical transformations in a single reaction vessel. In general, compounds formed as intermediates in the sequence are not isolated from a one-pot reaction mixture. Reagents necessary to affect the transformation sequence may be added together at the beginning of the sequence, or they may be added one after another (i.e., in a sequential manner) as the sequence progresses.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 20 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. An alkyl group, such as $C_1$-$C_{10}$ alkyl, may also include cycloalkyl groups such as cycloalkyl, such as cyclopropyl, cyclobutyl, cyclopentyl, cyclohexyl etc. . . .

As used herein, the term "protecting group" refers to a compound that renders a functional group unreactive, but is also removable so as to restore the functional group to its original state. Such protecting groups are well known to one of ordinary skill in the art and include compounds, for example, that are disclosed in Greene, T. W.; Wuts, P. G. M. *Protective Groups in Organic Synthesis*, 4th ed.; John Wiley & Sons, New York, 2006, which is incorporated herein by reference in its entirety.

Description of the Invention:

In one aspect, the present invention provides a process for the preparation of a compound of formula V,

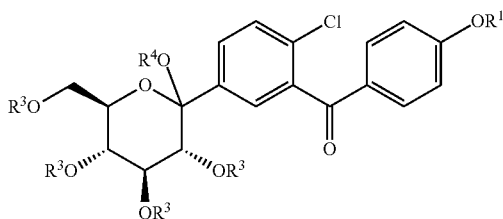

comprising the steps of:
i) converting a compound of formula II

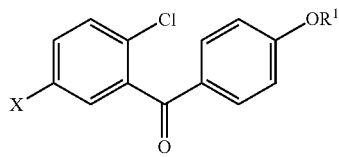

to a compound of formula III

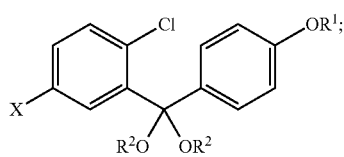

and
ii) contacting a compound of formula III with a compound of formula IV

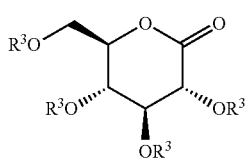

to form compound of formula V;
or
i') contacting a compound of formula II with a compound of formula IV to form a compound of formula V
wherein
X is a halogen;
$R^1$ is selected from the group consisting of (3S)-tetrahydro-3-furanyl, (3R)-tetrahydro-3-furanyl and $C_1$-$C_{10}$ alkyl;
$R^2$ is $C_1$-$C_{10}$ alkyl or can be taken together to form an optionally substituted 5-7 member cyclic ring;
$R^3$ is hydrogen or a hydroxyl protecting group; and
$R^4$ is $C_1$-$C_{10}$ alkyl.

In some embodiments, the compound of formula II is ketalized to form the compound of formula III, and then reacts with the compound of formula IV to form the compound of formula V. Preferably, $R^2$ of the compound of formula III is $C_1$-$C_{10}$ alkyl, for example, methyl, ethyl, isopropyl, or can be taken together to form an optionally substituted 5-7 member cyclic ring. More preferably, $R^2$ is methyl or taken together to form a heterocyclic ketal, such as dioxolane or 1,3-dioxane. In one aspect, the halogen is —Br, —Cl or —I. In another aspect, the halogen is —I.

In some embodiments, step i) is conducted in a solvent or solvent mixture in the presence of ketone protecting reagent and an acid to provide the compound of formula III, wherein the solvent is selected from the group consisting of dichloromethane (DCM), tetrahydrofuran (THF), 2-methyltetrahydrofuran (2-MeTHF), toluene and mixtures thereof, the ketone protecting reagent is selected from the group consisting of methanol, ethanol, 1,2-ethanediol, 1,3-propanediol and mixtures thereof, and the acid is selected from the group consisting of hydrochloric acid, trifluoromethanesulfonic acid, toluenesulfonic acid, methanesulfonic acid, sulfuric acid, phosphoric acid, camphorsulfonic acid and mixture thereof. In one aspect, the ketone protecting reagent is a mixture of trimethyl orthoformate and 1,2-ethanediol. In some embodiments, step ii) is conducted in a solvent or solvent mixture at about −80 to −60° C. for 1 to 2 hours in the presence of base to provide the compound of formula V, wherein the solvent is selected from the group consisting of THF, 2-MeTHF, toluene and mixtures thereof, and the base is selected from the group consisting of n-butyllithium, t-butyllithium, isopropylmagnesium chloride lithium chloride, tert-butylmagnesium chloride and mixtures thereof. More preferably, the base is n-butyllithium. In some embodiments, $R^3$ is hydrogen or a hydroxyl protecting group. Preferably, the $R^3$ is independently selected from the group consisting of benzyl, acetyl, benzoyl, $C_1$-$C_{12}$ alkyl, trialkylsilyl (such as trimethylsilyl or tert-butyl dimethyl silyl), allyl, and sulfonyl. More preferably, $R^3$ is benzoyl or trimethylsilyl.

In some embodiments, step ii) comprises the addition of $R^4$ group, which could be achieved in a solvent or solvent mixture at about 20 to 40° C. for 12 to 16 hours in the presence of an acid to provide the compound of formula V, wherein the solvent is selected from the group consisting of methanol, ethanol, isopropyl alcohol and mixtures thereof, and the acid is selected from the group consisting of methane sulfonic acid, p-toluene sulfonic acid, acetic acid, oxalic acid and mixtures thereof. More preferably, the acid is methane sulfonic acid. In some embodiments, the removal of $R^3$ groups is achieved along with the addition of $R^4$ group, especially when $R^3$ is a trialkylsilyl group. Preferably, $R^3$ is trimethylsilyl.

In step i') as shown above, the compound of formula II is directly reacted with the compound of formula IV to form the compound of formula V without ketalization. In some embodiments, step i') is conducted at about −80 to −60° C. for 1 to 2 hours in a solvent or solvent mixture in the presence of base to provide the compound of formula V, wherein the solvent is selected from the group consisting of THF, 2-MeTHF, toluene and mixtures thereof, and the base is selected from the group consisting of n-butyllithium, t-butyllithium, isopropylmagnesium chloride lithium chloride, tert-butylmagnesium chloride and mixtures thereof. More preferably, the base is n-butyllithium. In some embodiments, $R^3$ is hydrogen or a hydroxyl protecting group. Preferably, the $R^3$ is independently selected from the group consisting of benzyl, acetyl, benzoyl, $C_1$-$C_{12}$ alkyl, trialkylsilyl (such as trimethylsilyl or tert-butyl dimethyl silyl), allyl and sulfonyl. More preferably, $R^3$ is benzoyl or trimethylsilyl.

In some embodiments, step i') comprises the addition of $R^4$ group, which could be achieved in a solvent or solvent mixture at about 20 to 40° C. for 12 to 16 hours in the presence of acid to provide the compound of formula V, wherein the solvent is selected from the group consisting of methanol, ethanol, isopropyl alcohol and mixtures thereof, and the acid is selected from the group consisting of methane sulfonic acid, p-toluene sulfonic acid, acetic acid, oxalic acid and mixture thereof. More preferably, the acid is methane sulfonic acid. In some embodiments, the removal of $R^3$ groups is achieved along with the addition of $R^4$ group, especially when $R^3$ is a trialkylsilyl group. Preferably, $R^3$ is trimethylsilyl.

In a second aspect, the present invention further comprises converting the compound of formula V to a compound of formula I

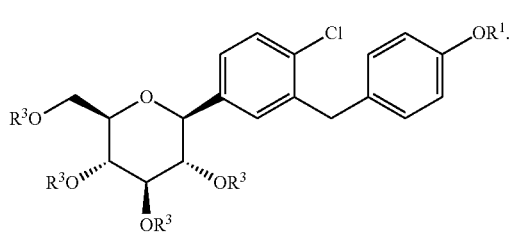

In some embodiments, the conversion from the compound of formula V to a compound of formula I comprises a successive 2-steps of reduction process in a one-pot reaction. In some embodiments, the first reduction step is conducted in a solvent or solvent mixture in the presence of a reducing agent. The solvent is selected from the group consisting of THF, 2-MeTHF, methanol, ethanol, isopropyl alcohol and mixtures thereof. In one embodiment, the reducing agent is a hydride and the hydride may be selected from the group consisting of $NaBH_4$, $LiAlH_4$, i-$Bu_2AlH$ and mixtures thereof. Preferably, the reducing agent is $NaBH_4$. The subsequent reduction step is then conducted in a solvent or solvent mixture in the presence of a reducing agent. The solvent is selected from the group consisting of DCM, chloroform, acetonitrile (ACN), toluene, THF, 2-MeTHF and mixtures thereof. In some embodiments, the solvent or solvent mixture is the same as used in the first reduction step. The reducing agent is selected from the group consisting of $Et_3SiH$, i-$Pr_3SiH$ and mixtures thereof. Preferably, the reducing agent is $Et_3SiH$. In one aspect, the reducing agent may be employed along with a Lewis acid, such as $BF_3.Et_2O$.

In a third aspect, the present invention further comprises
iii) converting compound of formula V to compound of formula VI

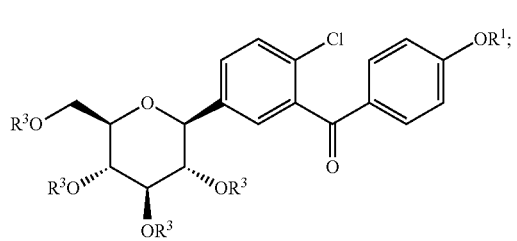

and
iv) converting compound of formula VI to compound of formula I.

In some embodiments, step iii) is conducted in a solvent or solvent mixture in the presence of a reducing agent. The solvent is selected from the group consisting of DCM, chloroform, ACN, toluene, THF, 2-MeTHF and mixtures thereof. The reducing agent may be a hydride, and the reducing agent is selected from the group consisting of $Et_3SiH$, i-$Pr_3SiH$ and mixture thereof. Preferably, the reducing agent is $Et_3SiH$. In one aspect, the reducing agent may be employed along with a Lewis acid, such as $BF_3.Et_2O$.

In some embodiments, step iv) comprises a successive 2-steps of reduction process in a one-pot reaction for the conversion of compound of formula VI to the compound of formula I. In some embodiments, the first reduction step is conducted in a solvent or solvent mixture in the presence of a reducing agent. The solvent is selected from the group consisting of THF, 2-MeTHF, methanol, ethanol, isopropyl alcohol and mixtures thereof. The reducing agent is a hydride, and is selected from the group consisting of $NaBH_4$, $LiAlH_4$, i-$Bu_2AlH$ and mixtures thereof. Preferably, the reducing agent is $NaBH_4$. The subsequent second reduction step is then conducted in a solvent or solvent mixture in the presence of a reducing agent. The solvent is selected from the group consisting of DCM, chloroform, ACN, toluene, THF, 2-MeTHF and mixtures thereof. In some embodiments, the solvent or solvent mixture is the same as used in the first reduction step. The reducing agent is selected from the group consisting of $Et_3SiH$, i-$Pr_3SiH$ and mixtures thereof. Preferably, the reducing agent is $Et_3SiH$. In one aspect, the reducing agent may be employed along with a Lewis acid, such as $BF_3.Et_2O$.

In a fourth aspect, the present invention provides a process for the preparation of a compound of formula I

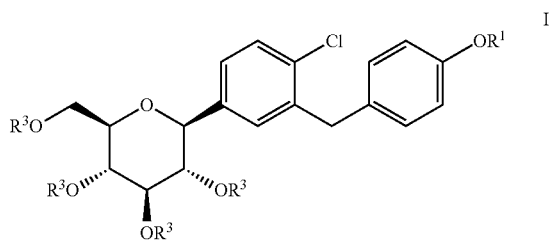

comprising the steps of:
i") converting a compound of formula II

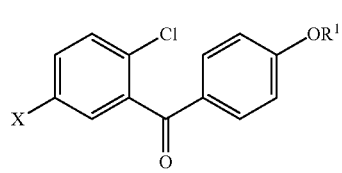

to a compound of formula VII

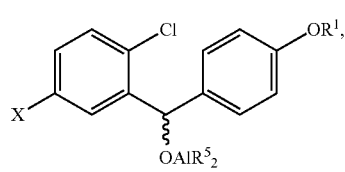

and
converting the compound of formula VII to a compound of formula VIII

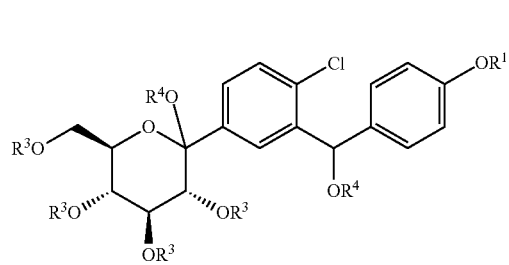

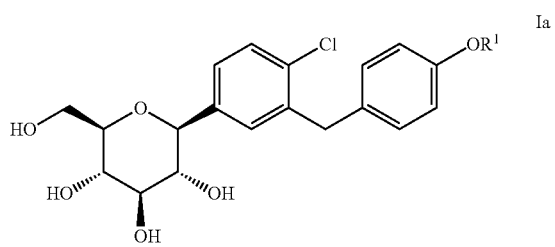

in a one-pot reaction; and ii″) converting the compound of VIII to compound of formula I wherein X is a halogen;

$R^1$ is selected from the group consisting of (3S)-tetrahydro-3-furanyl, (3R)-tetrahydro-3-furanyl and $C_1$-$C_{10}$ alkyl;

$R^3$ is hydrogen or hydroxyl protecting group; and $R^4$ and $R^5$ are $C_1$-$C_{10}$ alkyl.

In some embodiments, step i″) is conducted in a solvent or solvent mixture in the presence of a reducing agent to form the compound of formula VII, and then reacted with the compound of formula IV in the presence of a base to provide the compound of formula VIII in the presence of an acid in a one-pot reaction. For the preparation of compound of formula VII, the solvent is selected from the group consisting of THF, 2-MeTHF, toluene and mixtures thereof. The reducing agent is selected from the group consisting of $Me_2AlH$, $Et_2AlH$ or i-$Pr_2AlH$ and mixtures thereof. Preferably, the reducing agent is i-$Pr_2AlH$. For the reaction between the compound of formula VII with the compound of formula IV, the base is selected from the group consisting of n-butyllithium, t-butyllithium, isopropylmagnesium chloride lithium chloride, tert-butylmagnesium chloride and mixtures thereof. Preferably, the base is n-butyllithium. In some embodiments, step ii″) is conducted in a solvent or solvent mixture in the presence of a reducing agent. The solvent is selected from the group consisting of DCM, chloroform, ACN, toluene, THF, 2-MeTHF and mixtures thereof. The reducing agent is selected from the group consisting of $Et_3SiH$, i-$Pr_3SiH$ and mixtures thereof. Preferably, the reducing agent is $Et_3SiH$.

In some embodiments, step i″) comprises the addition of $R^4$ group, which could be achieved in a solvent or solvent mixture at about 20 to 40° C. for 12 to 16 hours in the presence of acid to provide the compound of formula VIII, wherein the solvent is selected from the group consisting of methanol, ethanol, isopropylalcohol or mixtures thereof. Preferably, the solvent is methanol. The acid is selected from the group consisting of methane sulfonic acid, p-toluene sulfonic acid, acetic acid, oxalic acid and mixture thereof. More preferably, the acid is methane sulfonic acid. In some embodiments, the removal of $R^3$ groups is achieved along with the addition of $R^4$ group, especially when $R^3$ is a trialkylsilyl group. Preferably, $R^3$ is trimethylsilyl.

In some embodiments, the present invention further comprises converting the compound of formula I to the compound of formula Ia where for the compound of formula I, $R^3$ is not hydrogen.

Hydrolysis of the compound of formula I to the compound of formula Ia is conducted in the presence of a base or an acid. Preferably, the base is selected from the group consisting of LiOH, LiOOH, NaOH, NaOOH or KOH. More preferably, the base is LiOH. In one aspect, the hydrolysis may be performed in a solvent selected from the group consisting of THF, 2-MeTHF, MeOH, EtOH, isopropyl alcohol, $H_2O$ or mixtures thereof.

In some embodiments, the compound of formula Ia is dapagliflozin or empagliflozin.

In yet another aspect of the present invention provides a compound of formula III

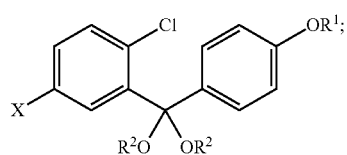

wherein X is a halogen; $R^1$ is selected from the group consisting of (3S)-tetrahydro-3-furanyl, (3R)-tetrahydro-3-furanyl and $C_1$-$C_{10}$ alkyl; and $R^2$ is $C_1$-$C_{10}$ alkyl or can be taken together to form an optionally substituted 5-7 member cyclic ring. In one aspect, $R^2$ is $C_1$-$C_{10}$ alkyl; and $C_1$-$C_{10}$ alkyl is selected from the group consisting of methyl, ethyl, propyl, butyl, iso-butyl, pentyl, iso-pentyl, hexyl, heptyl, octyl, nonyl and decanyl.

In another aspect of the present invention provides a compound of formula V

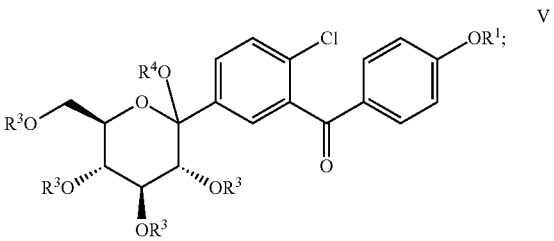

wherein $R^1$ is selected from the group consisting of (3S)-tetrahydro-3-furanyl, (3R)-tetrahydro-3-furanyl and $C_1$-$C_{10}$ alkyl; $R^3$ is hydrogen or hydroxyl protecting group; and $R^4$ is $C_1$-$C_{10}$ alkyl.

In another aspect of the present invention provides a compound of formula VI

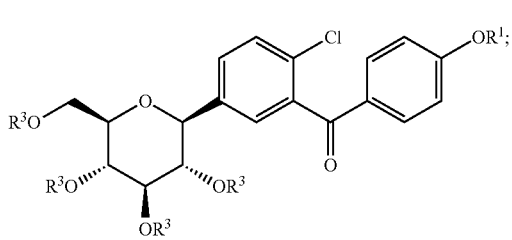

wherein R¹ is selected from the group consisting of (3S)-tetrahydro-3-furanyl, (3R)-tetrahydro-3-furanyl and $C_1$-$C_{10}$ alkyl; and R³ is hydrogen or hydroxyl protecting group.

In another aspect of the present invention provides a compound of formula VIII

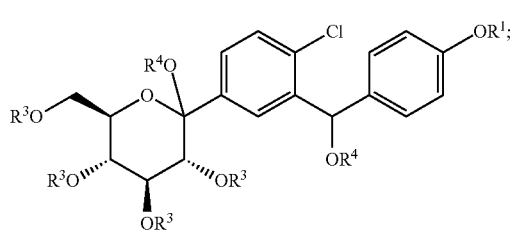

wherein R¹ is selected from the group consisting of (3S)-tetrahydro-3-furanyl, (3R)-tetrahydro-3-furanyl and $C_1$-$C_{10}$ alkyl; R³ is hydrogen or hydroxyl protecting group; and R⁴ is $C_1$-$C_{10}$ alkyl.

In addition to the exemplary embodiments, aspects and variations described above, further embodiments, aspects and variations will become apparent by reference to the drawings and figures and by examination of the following descriptions.

The foregoing examples of the related art and limitations are intended to be illustrative and not exclusive. Other limitations of the related art will become apparent to those of skill in the art upon a reading of the specification and a study of the drawings or figures as provided herein.

EXAMPLES

The following examples are provided to further illustrate, but not to limit this invention.

Example 1

Preparation of 2-(2-chloro-5-iodo-phenyl)-2-[4-[(3S)-tetrahydrofuran-3-yl]oxyphenyl]-1,3-dioxolane

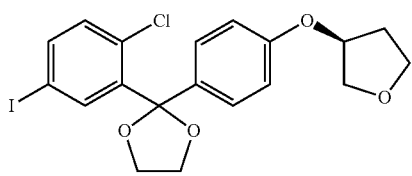 [SMILES: Clc1ccc(I)cc1C1(c2ccc(O[C@H]3CCOC3)cc2)OCCO1]

(2-Chloro-5-iodo-phenyl)-[4-[(3R)-tetrahydrofuran-3-yl]oxyphenyl]methanone (10 g, 23.3 mmol, 1.0 equiv.), trimethyl orthoformate (12.8 mL, 117 mmol, 5.0 equiv.) and 1,2-ethanediol (13 mL, 233 mmol, 10.0 equiv.) were mixed and cooled to 0° C. Trifluoromethanesulfonic acid (0.4 mL, 5 mmol, 0.2 equiv.) was added and the reaction mixture was heated to 90-95° C. and monitored. After the reaction was complete, the reaction mixture was cooled to 0-5° C. and quenched by slow addition of 25% NaOH. After being extracted 3× with EtOAc, the organic portion was washed with $H_2O$, sat'd aq $NaHCO_3$ and brine. The resultants were concentrated to give a crude oil. The residues were crystallized from IPA and yielded 10 g of title compound as a white solid which was used directly for the next step without further purification.

Example 2

Preparation of [2-chloro-5-[(3R,4S,5S,6R)-3,4,5-trihydroxy-6-(hydroxymethyl)-2-methoxy-tetrahydropyran-2-yl]phenyl]-[4-[(3S)-tetrahydrofuran-3-yl]oxyphenyl]methanone

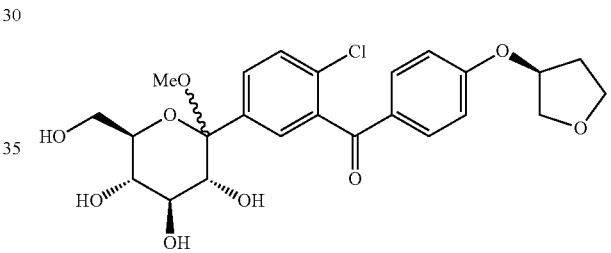

To a solution of 2-(2-chloro-5-iodo-phenyl)-2-[4-[(3S)-tetrahydrofuran-3-yl]oxyphenyl]-1,3-dioxolane (8.14 g, 17.2 mmol, 1.1 equiv.) in 2-MeTHF (73 mL) was cooled to −78° C. and added 2,3,4,6-tetrakis-O-trimethylsilyl-D-gluconolactone (7.5 mL, 16 mmol, 1.0 equiv.) followed by dropwise addition of 2.1 M n-butyllithium/hexane (9.8 mL, 21 mmol, 1.3 equiv., 9.8 mL). After stirring at −78° C. for 2 h, a solution of methane sulfonic acid (0.9 mL, 10.0 mmol, 4.0 equiv.) in methanol (19 mL) was added. The cooling bath was then removed, and the resultants were stirred at ambient temperature for 16 h. An additional methanesulfonic acid (0.5 mL, 8 mmol, 0.5 equiv.) was added and the reaction mixture was heated to 45° C. for another 4 h. After the reaction was complete, the reaction mixture was quenched by sat'd aq $NaHCO_3$ until pH>7. The resultants were concentrated to remove the organic solvents prior to being extracted 3× with EtOAc. The combined organic layers were washed with brine and dried over $Na_2SO_4$. After concentration the crude oil was purified by column chromatography to yield 5.3 g of the title compound as a white solid.

Example 3

Preparation of [2-chloro-5-[(3R,4R,5S,6R)-3,4,5-trihydroxy-6-(hydroxymethyl)tetrahydropyran-2-yl]phenyl]-[4-[(3S)-tetrahydrofuran-3-yl]oxyphenyl]methanone

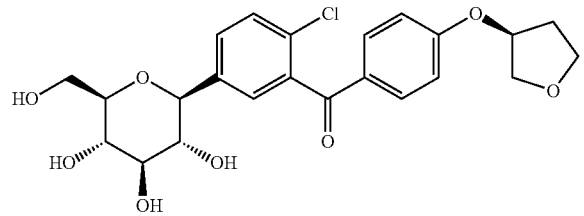 [SMILES: O=C(c1ccc(O[C@H]2CCOC2)cc1)c1cc([C@@H]2O[C@H](CO)[C@@H](O)[C@H](O)[C@H]2O)ccc1Cl]

To a solution of [2-chloro-5-[(3R,4S,5S,6R)-3,4,5-trihydroxy-6-(hydroxymethyl)-2-methoxy-tetrahydropyran-2-yl]phenyl]-[4-[(3S)-tetrahydrofuran-3-yl]oxyphenyl]methanone (1.6 g, 3.2 mmol, 1.0 equiv.) in DCM (16 mL) and ACN (16 mL) was added $Et_3SiH$ (2.3 mL, 14 mmol, 4.5 equiv.) and followed by $BF_3Et_2O$ (1.3 mL, 11 mmol, 3.3 equiv.) at such rate that temperature did not exceed ≤−15° C. The stirred solution was allowed to warm to 0-5° C. over 2 h. When HPLC analysis indicated the reaction was complete, the reaction was quenched by addition of EtOAc and sat'd aq $NaHCO_3$. The resultants were concentrated to remove the organic solvents prior to being extracted 3× with EtOAc. The combined organic layers were washed with brine and dried over $Na_2SO_4$. After concentration the crude oil was purified by column chromatography to yield 1.28 g of the title compound as a white solid.

Example 4

Preparation of (2S,3R,4R,5S,6R)-2-[4-chloro-3-[[4-[(3S)-tetrahydrofuran-3-yl]oxyphenyl]methyl]phenyl]-6-(hydroxymethyl)tetrahydropyran-3,4,5-triol

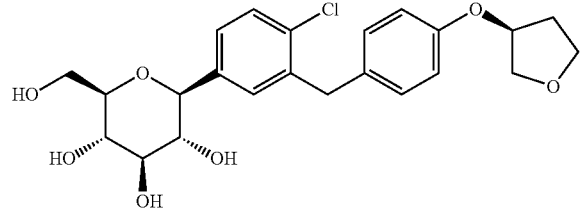 [SMILES: OC[C@H]1O[C@@H](c2ccc(Cl)c(Cc3ccc(O[C@H]4CCOC4)cc3)c2)[C@H](O)[C@@H](O)[C@@H]1O]

To a suspension of (2S,3R,4R,5S,6R)-2-[4-chloro-3-[[4-[(3S)-tetrahydrofuran-3-yl]oxyphenyl]methyl]phenyl]-6-(hydroxymethyl)tetrahydropyran-3,4,5-triol (100 mg, 0.215 mmol, 1.0 equiv.) in THF (2 mL) at 0° C. was slowly added $NaBH_4$ (16.3 mg, 0.431 mmol, 2.0 equiv.). The reaction mixture was stirred at 0° C. for 0.5 h and at RT for 1 h, and then quenched with $H_2O$ at 0° C. The resultants were extracted 2× with EtOAc. The combined organic layers were washed with brine and dried over $Na_2SO_4$. After concentration the obtained crude white solid was dissolved in DCM (1 mL) and ACN (1 mL) and added $Et_3SiH$ (80 µL, 0.501 mmol, 2.34 equiv.) and followed by $BF_3Et_2O$ (66 µL, 0.535 mmol, 2.50 equiv.) at 0-5° C. When HPLC analysis indicated the reaction was complete, the reaction was quenched by addition of EtOAc and sat'd aq $NaHCO_3$. The resultants were concentrated to remove the organic solvents prior to being extracted 3× with EtOAc. The combined organic layers were washed with brine and dried over $Na_2SO_4$. After concentration the crude oil was crystallization from IPAc to yield 81 mg of the title compound as a white solid.

Example 5

Preparation of methyl 1-C-[4-chloro-3-[(4-ethoxyphenyl) methoxymethyl] phenyl] D-glucopyranoside

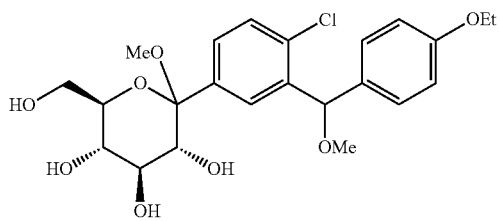 [SMILES: CCOc1ccc(C(OC)c2cc(C3(OC)O[C@H](CO)[C@@H](O)[C@H](O)[C@H]3O)ccc2Cl)cc1]

To a solution of (2-chloro-5-iodo-phenyl)-(4-ethoxyphenyl) methanone (9.1 g, 24 mmol, 1.1 equiv.) in 2-MeTHF (100 mL) was cooled to 0-5° C. and followed by dropwise addition of DIBAL-H (26 mL, 26 mmol, 1.2 equiv). After the reaction was complete, the reaction mixture was cooled to −78° C. and added 2,3,4,6-tetrakis-O-trimethylsilyl-D-gluconolactone (10 g, 21.4 mmol, 1.0 equiv) followed by dropwise addition of 2.1 M n-butyllithium/hexane (13 mL, 27 mmol, 1.3 equiv). After stirring at −78° C. for 2 h, a solution of methane sulfonic acid (15.3 mL, 236 mmol, 11.0 equiv.) in methanol (30 mL) was added. The cooling bath was then removed, and the resultants were stirred at ambient temperature for 16 h. After the reaction was complete, the reaction mixture was quenched by sat'd aq $NaHCO_3$. The resultants were concentrated to remove the organic solvents prior to being extracted with EtOAc. The combined organic layers were washed with brine and dried over $Na_2SO_4$. After concentration the crude oil was purified by column chromatography to yield 5.7 g (57%) of the title compound as a white solid.

Example 6

Preparation of methyl 1-C-[4-chloro-3-[(4-ethoxyphenyl) methoxymethyl] phenyl]-, 2, 3, 4, 6-tetrabenzoate D-glucopyranoside

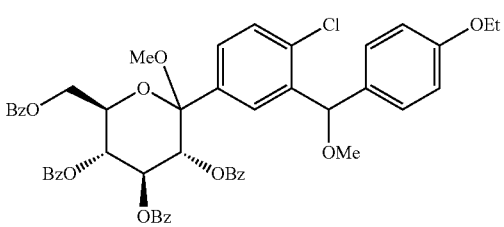

To a solution of methyl 1-C-[4-chloro-3-[(4-ethoxyphenyl) methoxymethyl] phenyl] D-glucopyranoside (2.0 g, 4.3 mmol, 1.0 equiv.) in DCM (60 mL) was cooled to 0-5° C. and added triethylamine (4.2 mL, 30.0 mmol, 7.1 eq)

followed by addition of 4-dimethylaminopyridine (525 mg, 4.3 mmol, 1.0 eq). After stirring at 0-5° C. for 20 min, benzoyl chloride (3 mL, 25.8 mmol, 6.05 eq) was dropwise added. After the reaction was complete, the reaction mixture was quenched by 0.5N HCl until pH<3 and stirred at 20-30° C. for extraction. The organic phase was washed with sat'd aq NaHCO₃ until pH>8. After concentration the crude oil was purified by column chromatography to yield as a white solid.

Example 7

Preparation of 1,5-anhydro-1-C-[4-chloro-3-[(4-ethoxyphenyl) methyl] phenyl]-, 2, 3, 4, 6-tetrabenzoate, (1S) D-Glucitol

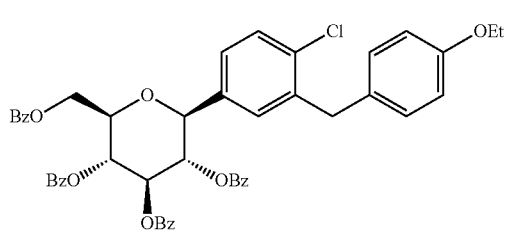

To a solution of methyl 1-C-[4-chloro-3-[(4-ethoxyphenyl) methoxymethyl] phenyl]-, 2, 3, 4, 6-tetrabenzoate D-glucopyranoside (200 mg, 0.23 mmol, 1.0 equiv.) in ACN (60 mL) containing H₂O (4.1 µL, 0.23 mmol, 1.0 equiv). The reaction mixture was added Et₃SiH (0.22 mL, 1.4 mmol, 6.1 equiv) followed by dropwise addition of BF₃.Et₂O (0.13 mL, 1.01 mmol, 4.5 equiv). The reaction mixture was heated to 40° C. After the reaction was complete, the reaction mixture was quenched by sat'd aq NaHCO₃. The reaction mixture was extracted three times with EtOAc. The organic layers were drying over MgSO₄ and concentrated under vacuum to crude oil of 1,5-anhydro-1-C-[4-chloro-3-[(4-ethoxyphenyl) methyl] phenyl]-, 2, 3, 4, 6-tetrabenzoate, (1S) D-Glucitol.

Example 8

Preparation of (2S,3R,4R,5S,6R)-2-(4-chloro-3-(4-ethoxybenzyl)phenyl)-6-(hydroxymethyl)tetrahydro-2H-pyran-3,4,5-triol

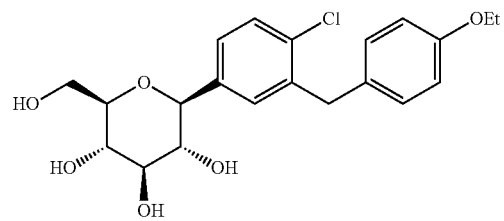 [SMILES: CCOc1ccc(Cc2cc([C@@H]3O[C@H](CO)[C@@H](O)[C@H](O)[C@H]3O)ccc2Cl)cc1]

To a solution of methyl 1,5-anhydro-1-C-[4-chloro-3-[(4-ethoxyphenyl) methyl] phenyl]-, 2, 3, 4, 6-tetrabenzoate, (1S) D-Glucitol (186 mg, 0.23 mmol, 1.0 equiv.) in THF/MeOH/H₂O (4 mL, 2:3:1) and added lithium hydroxide monohydrate (12 mg, 0.29 mmol, 1.3 eq). After stirring overnight, the solvent was removed under vacuum. The mixture was dissolved in EtOAc and washed with brine prior to drying over MgSO₄. The organic layer was concentrated under vacuum to afford the (2S,3R,4R,5S,6R)-2-(4-Chloro-3-(4-ethoxybenzyl)phenyl)-6-(hydroxymethyl)tetrahydro-2H-pyran-3,4,5-triol.

Example 9

Preparation of (2S,3R,4R,5S,6R)-2-(4-chloro-3-(4-ethoxybenzyl)phenyl)-6-(hydroxymethyl)tetrahydro-2H-pyran-3,4,5-triol

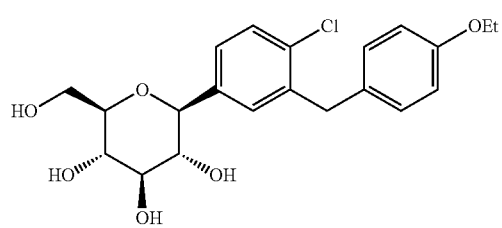 [SMILES: CCOc1ccc(Cc2cc([C@@H]3O[C@H](CO)[C@@H](O)[C@H](O)[C@H]3O)ccc2Cl)cc1]

To a solution of methyl 1-C-[4-chloro-3-[(4-ethoxyphenyl) methoxymethyl] phenyl] D-glucopyranoside (200 mg, 4.3 mmol, 1.0 equiv.) in DCM/ACN (2 mL, 1:1) and added Et₃SiH (0.28 mL, 1.8 mmol, 4.1 equiv) at 0-5° C. The mixture was added BF₃.Et₂O (0.08 mL, 0.65 mmol, 1.5 eq) at this temperature. After the reaction was complete, the reaction mixture was quenched by sat'd aq NaHCO₃. The reaction mixture was extracted three times with EtOAc. The organic layers were dried over MgSO₄ and concentrated under vacuum to a crude oil of (2S,3R,4R,5S,6R)-2-(4-Chloro-3-(4-ethoxybenzyl)phenyl)-6-(hydroxymethyl)tetrahydro-2H-pyran-3,4,5-triol.

What is claimed is:

1. A process for the preparation of a compound of formula V,

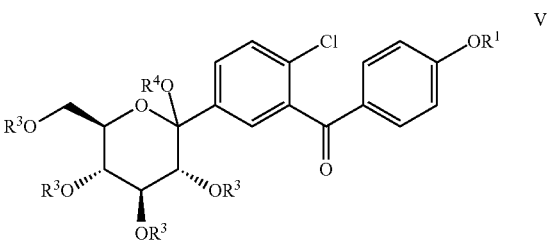

comprising the steps of:
i) converting a compound of formula II

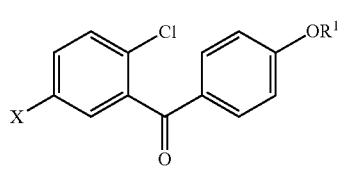

to a compound of formula III

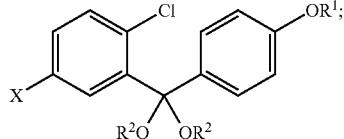

and ii) contacting the compound of formula III with a compound of formula IV

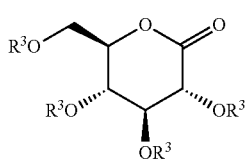

to form the compound of formula V;

or i') contacting the compound of formula II with the compound of formula IV to form the compound of formula V wherein X is a halogen;

R$^1$ is selected from the group consisting of (3S)-tetrahydro-3-furanyl, (3R)-tetrahydro-3-furanyl and C$_1$-C$_{10}$ alkyl;

R$^2$ is C$_1$-C$_{10}$ alkyl or can be taken together to form an optionally substituted 5-7 member cyclic ring;

R$^3$ is hydrogen or a hydroxyl protecting group; and

R$^4$ is C$_1$-C$_{10}$ alkyl.

2. The process of claim 1, wherein step i) is conducted in the presence of a ketone protecting group, which is selected from the group consisting of methanol, ethanol, 1,2-ethanediol, 1,3-propanediol and mixture thereof.

3. The process of claim 1, wherein steps ii) and i') are conducted in the presence of a base, which is selected from the group consisting of n-butyllithium, t-butyllithium, isopropylmagnesium chloride lithium chloride, tert-butylmagnesium chloride and mixtures thereof.

4. The process of claim 3, further comprising adding an acid, which is selected from the group consisting of methane sulfonic acid, p-toluene sulfonic acid, acetic acid, oxalic acid and mixture thereof.

5. The process of claim 1, further comprising converting the compound of formula V to a compound of formula I

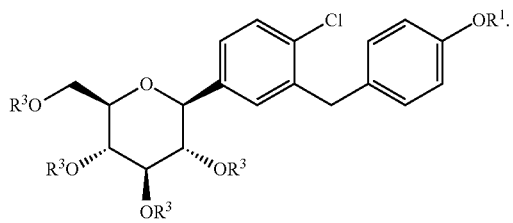

6. The process of claim 5, further comprising converting the compound of formula I to compound of formula Ia

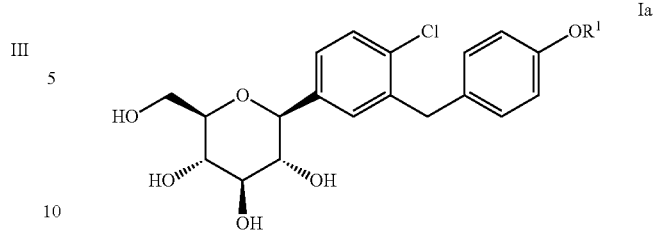

where for the compound of formula I, R$^3$ is not hydrogen.

7. The process of claim 6, wherein the compound of formula Ia is selected from the group consisting of dapagliflozin and empagliflozin.

8. The process of claim 5, wherein the conversion is a one-pot reaction comprising:

A) first reduction step, which is conducted in the presence of a reducing agent selected from the group consisting of NaBH$_4$, LiAlH$_4$, i-Bu$_2$AlH and mixtures thereof; and B) second reduction step, which is conducted in the presence of a reducing agent selected from the group consisting of Et$_3$SiH, i-Pr$_3$SiH and mixtures thereof.

9. The process of claim 1, further comprising:

iii) converting the compound of formula V to a compound of formula VI

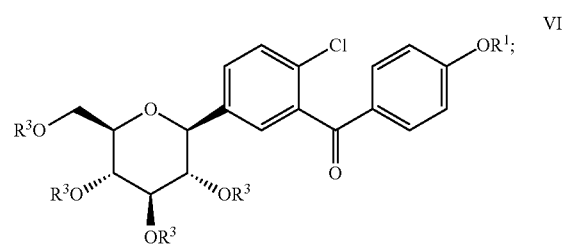

and iv) converting the compound of formula VI to the compound of formula I

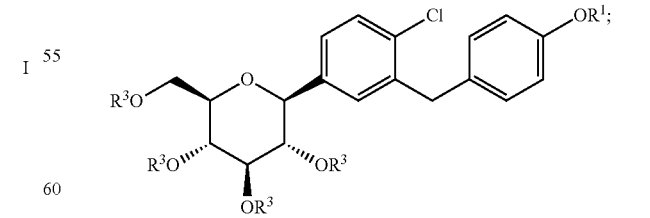

and v) converting the compound of formula I to the compound of formula Ia

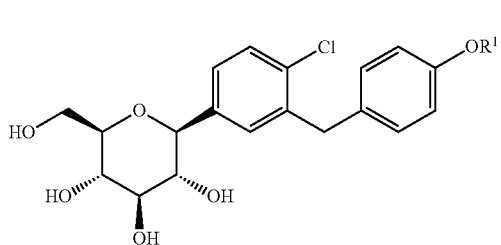

where for the compound of formula I, $R^3$ is not hydrogen.

10. The process of claim 9, wherein step iii) is conducted in the presence of a reducing agent selected from the group consisting of $NaBH_4$, $LiAlH_4$, $i\text{-}Bu_2AlH$ and mixtures thereof.

11. The process of claim 9, wherein the compound of formula Ia is selected from the group consisting of dapagliflozin and empagliflozin.

12. The process of claim 9, step iv) is a one-pot reaction comprising:
A) first reduction step, which is conducted in the presence of a reducing agent selected from the group consisting of $NaBH_4$, $LiAlH_4$, $i\text{-}Bu_2AlH$ and mixtures thereof; and
B) second reduction step, which is conducted in the presence of a reducing agent selected from the group consisting of $Et_3SiH$, $i\text{-}Pr_3SiH$ and mixtures thereof.

13. A compound of formula V

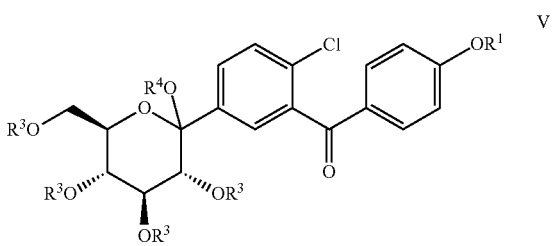

wherein $R^1$ is selected from the group consisting of (3S)-tetrahydro-3-furanyl, (3R)-tetrahydro-3-furanyl and $C_1$-$C_{10}$ alkyl;

$R^3$ is hydrogen or hydroxyl protecting group; and $R^4$ is $C_1$-$C_{10}$ alkyl.

* * * * *